United States Patent [19]

Brown et al.

[11] 4,321,379

[45] Mar. 23, 1982

[54] 4-ARYL-1-OXA-8-AZASPIRO[4,5]DEC-3-EN-2-ONES

[75] Inventors: John J. Brown, New City, N.Y.; Robert A. Hardy, Jr., Ridgewood, N.J.

[73] Assignee: American Cyanamid Company, Stamford, Conn.

[21] Appl. No.: 229,043

[22] Filed: Jan. 28, 1981

[51] Int. Cl.$^3$ .................................... C07D 491/107
[52] U.S. Cl. .................................... 546/16; 424/267
[58] Field of Search ........................ 546/16

[56] References Cited

PUBLICATIONS

Boyer et al. "Chim. Ther." (1970) vol. 5, No. 2, pp. 105–110.
Wittekind et al. "J. Heterocyclic Chem." (1972) vol. 9, No. 1, pp. 111–113.
Bennett "Chem. Lett." (1975) No. 9, pp. 939–942.

Primary Examiner—Robert T. Bond
Attorney, Agent, or Firm—Edward A. Conroy, Jr.

[57] ABSTRACT

This disclosure describes 8-substituted-4-phenyl-1-oxa-8-azaspiro[4,5]dec-3-en-2-ones and 8-substituted-4-phenyl-1-oxa-8-azaspiro[4,5]decan-2-ones useful as analgesic or neuroleptic agents.

14 Claims, No Drawings

4-ARYL-1-OXA-8-AZASPIRO[4,5]DEC-3-EN-2-ONES

BRIEF SUMMARY OF THE INVENTION

This invention relates to new organic compounds and, more particularly, is concerned with novel 8-substituted 4-aryl-1-oxa-8-azaspiro[4,5]-decan-2-ones (A) and 8-substituted-4-aryl-1-oxa-8-azaspiro[4,5]-dec-3-en-2-ones (B) which may be represented by the following structural formulae:

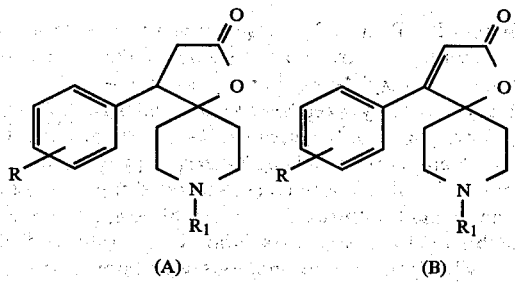

wherein R is hydrogen, fluoro, chloro or trifluoromethyl, and $R_1$ is hydrogen, alkyl having up to 4 carbon atoms, alkanoyl having up to 4 carbon atoms, alkenyl having from 3 to 6 carbon atoms, cycloalkylmethyl having from 4 to 7 carbon atoms, phenylalkyl having from 7 to 10 carbon atoms, ω-benzoylalkyl having up to 4 carbon atoms in the alkyl moiety, ω-(p-fluorophenyl)alkyl having up to 4 carbon atoms in the alkyl moiety, ω-di(p-fluorophenyl)alkyl having up to 4 carbon atoms in the alkyl moiety or ω-(p-fluorobenzoyl)alkyl having up to 4 carbon atoms in the alkyl moiety. Suitable alkyl and alkanoyl groups contemplated by the present invention are, for example, methyl, ethyl, isopropyl, sec-butyl, isobutyl, acetyl, propionyl, and the like. Suitable alkenyl groups may be, for example, allyl, methallyl, isopropenyl, 1-butenyl, crotyl, 3-butenyl, etc. whereas appropriate cycloalkylmethyl groups are cyclopropylmethyl, cyclobutylmethyl, cyclopentylmethyl and cyclohexylmethyl. Phenylalkyl is exemplified by benzyl, α-phenethyl, β-phenethyl, α-methyl-β-phenethyl, β-methyl-βphenethyl, 3-phenyl-2-methyl-propyl, 4-phenylbutyl, and the like.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are capable of forming acid-addition salts with a variety of organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The novel 8-substituted-4-phenyl-1-oxa-8-azaspiro[4,5]dec-3-en-2-ones of the present invention may be readily prepared as set forth in the following reaction scheme:

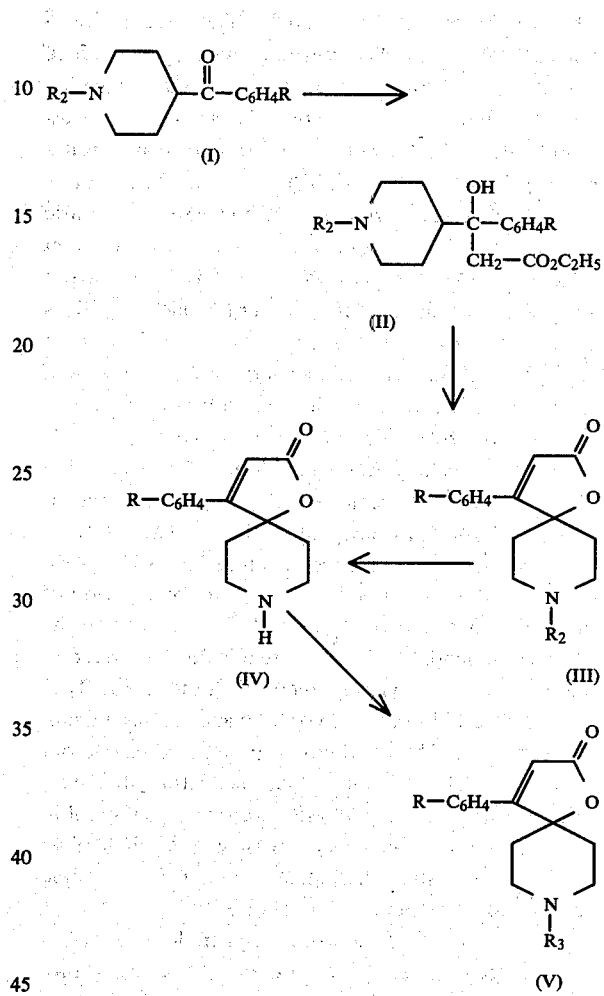

wherein R is hydrogen, fluoro, chloro, or trifluoromethyl, and $R_2$ is alkanoyl having up to 4 carbon atoms or carboalloxy having up to 4 carbon atoms and $R_3$ is alkyl having up to 4 carbon atoms, alkenyl having from 3 to 6 carbon atoms, cycloalkylmethyl having from 4 to 7 carbon atoms, phenylalkyl having from 7 to 10 carbon atoms, ω-benzoylalkyl having from 8 to 11 carbon atoms, ω-(p-fluorophenyl)alkyl having from 7 to 10 carbon atoms, ω-di(p-fluorophenyl)alkyl having from 13 to 16 carbon atoms or ω-(p-fluorobenzoyl)alkyl having from 8 to 11 carbon atoms. Suitable alkanoyl blocking groups contemplated by the present invention are acetyl, propionyl, isobutylryl, and the like. Suitable carboalkoxy blocking groups contemplated by the present invention are carbomethoxy, carbethoxy, carbo-n-propoxy and carboisopropoxy.

In accordance with the above reaction scheme, an appropriately substituted phenyl 4-piperidyl ketone (I) is converted to the corresponding 1-substituted-β-(phenyl)-4-piperidinehydracrylic acid ethyl ester (II) by means of the Reformatsky reaction with ethyl bromacetate. The phenyl 4-piperidyl ketones (I) are readily obtained by methods well known in the art as set forth by Duncan et al., J. Med. Chem. 13, 1(1970). The Reformatsky conversion to the piperidyl carbinols (II) is also accomplished by standard procedures as disclosed by Shriner, Organic Reactions 1,(1942); Diaper et al., Chem. Revs. 59, 89(1959); and Rathke, Organic Reactions 22, 423(1975). The rearrangement/cyclization of the piperidyl carbinols (II) with concomitant oxidation then provides the 8-substituted-4-aryl-1-oxa-8-azaspiro[4,5]dec-3-en-2-ones (III), also described as "unsaturated spirolactones". This reaction is best carried out by stirring a piperidyl carbinol (II) is concentrated sulfuric acid at an elevated temperature to effect concomitant oxidation. The temperature range is from about 75°–100° C. Isolation of the unsaturated lactone (III) is readily achieved by pouring the reaction mixture onto ice and extracting the product into an organic solvent such as chloroform, methylene chloride, or ethyl acetate followed by evaporation of the solvent.

The N-dealkanoylation and N-decarboalkoxylation of the unsaturated lactones (III) to provide the 4-(phenyl)-1-oxa-8-azaspiro[4,5]dec-3-en-2-ones (IV) is accomplished by hydrolysis in dilute 3 N-6 N hydrochloric acid at steam bath temperature for a period of time of 5–15 hours. Alkylation of (IV) to provide the novel compounds (V) of the present invention is accomplished with an alkylating agent of the formula: $R_3$-X wherein X is chloro, bromo or iodo and $R_3$ is as hereinabove defined. This alkylation is preferably carried out in an inert solvent such as benzene, tetrahydrofuran, toluene, or dioxane at the reflux temperature thereof in the presence of an acid-acceptor such as triethylamine, anhydrous potassium carbonate, N-methylmorpholine or soda ash for a period of time of 5–15 hours.

The novel 8-substituted-4-phenyl-1-oxa-8-azaspiro[4,5]decan-2-ones of the present invention are prepared as set forth in the following scheme:

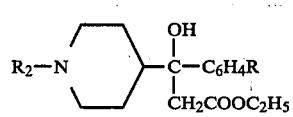

(II)

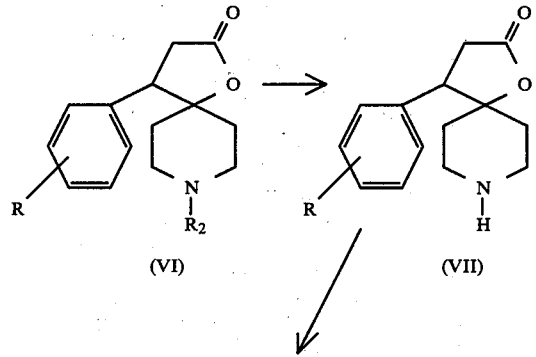

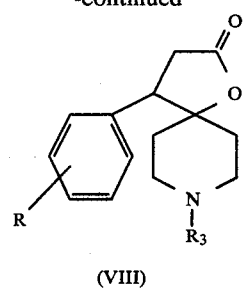

(VIII)

wherein $R_1$, $R_2$ and $R_3$ are as defined above. In accordance with the above reaction scheme, the same 1-substituted-$\beta$-phenyl-4-piperidinehydracrylic acid esters, (II, above) are cyclized/rearranged under acidic conditions without concomitant oxidation to provide the 8-substituted-4-phenyl-1-oxa-8-azaspiro[4,5]decan-2-ones (VI), also described as "saturated spirolactones." Concentrated sulfuric acid at room temperature is a suitable cyclizing agent. Isolation of the saturated lactone VI is achieved by methods well known to those skilled in the art. Partition chromatography is an effective method of isolating the product. In some cases, the above described cyclization with sulfuric acid also produces, as a minor by-product, the 4-(indanylidene)-piperidine IX.

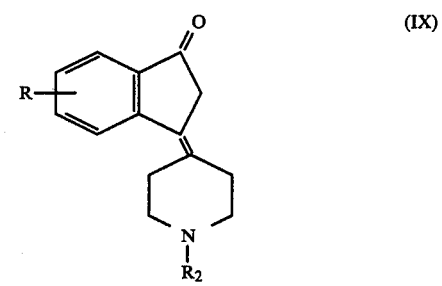

wherein R and $R_2$ are as previously described. Separation of the saturated lactone VI from the indanylidenepiperidine IX is readily accomplished by partition chromatography on a Celite ® diatomaceous earth column using a hexane-methanol solvent system.

N-dealkanoylation and N-decarboalkoxylation of the saturated lactones VI to the corresponding N-nor compounds VII and alkylation to the novel saturated compounds VIII of the present invention is carried out in exactly the same manner as described above for the unsaturated lactones (III→IV→V).

An alternate scheme for synthesis of the novel 8-substituted-4-phenyl-1-oxa-8-azaspriro[4,5]decan-2-ones of the present invention is illustrated as follows:

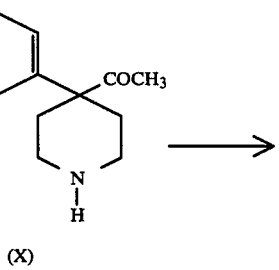

(X)

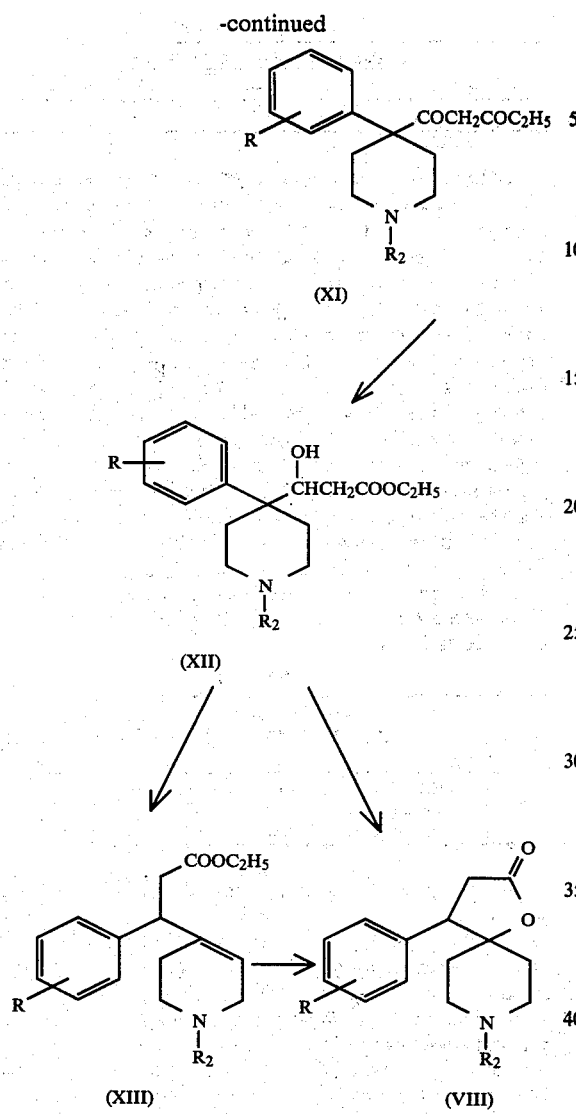

are suitable for this converstion. This intermediate is formed by a Wagner-Meerwein shift of the phenyl group. Cyclization of the unsaturated ester (XIII) to the saturated lactones (VIII) of this invention is then effected by treatment with sulfuric acid as described above. The unsaturated ester (XIII) may, therefore, be considered an intermediate which is formed in situ and which may, under some conditions, be isolated as such, and which may also be converted to the lactones of this invention (both III and VIII) without isolation.

The unsaturated ester XIV (isomeric with XIII) and the unsaturated hydroxy ester XV are also un-isolated, in situ intermediates which may be formed during the oxidative cyclization process which takes place in sulfuric acid at elevated temperatures (and described above, in detail); XV then cyclizes directly to the unsaturated spirolactone (III).

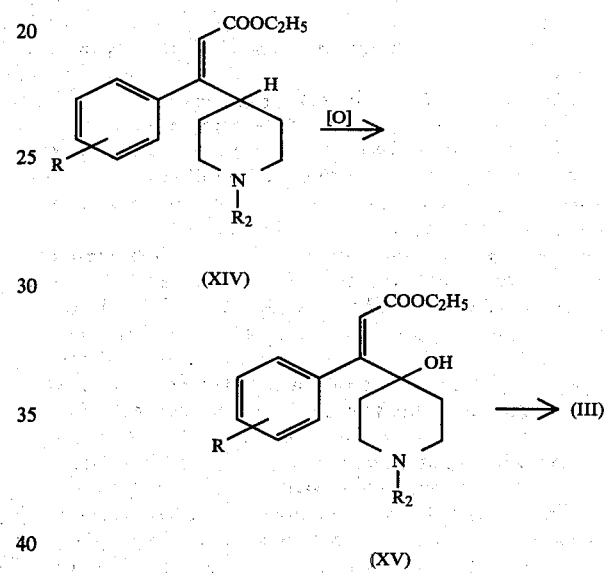

The variety of conditions appropriate for these conversions are illustrated in greater detail in the specific disclosure.

wherein R and $R_2$ are as described above. By this method, the 4-phenyl-4-acetylpiperidine (X), known to the art (or commercially available), is transformed to the β-keto-ester (XI) by standard procedures. Diethyl carbonate and sodium hydride in an inert solvent such as benzene, toluene and the like are suitable. Reduction of the keto ester then gives the hydroxy ester (XII), a 4-phenyl-4-piperidinehydracrylic ester. Sodium borohydride in ethanol is a suitable reducing agent.

Conversion and cyclization of the 4-phenyl-4-piperidinehydracrylic ester (XII) to the novel compounds of this invention may be effected in several ways. Treatment of XII with polyphosphoric acid for several hours gives the saturated lactone VIII. The temperature is from about 50°-100° C. Treatment of XII with sulfuric acid, as described above, also gives the saturated lactone (VIII), sometimes admixed with the above described indanylidene-piperidine IX. Partition chromatography is an effective method in separating these reaction products in a pure state. Alternatively, dehydration of the 4-phenyl-4-piperidine hydracrylic ester (XII) may produce the unsaturated ester XIII, identified by its spectral characteristics. N-bromoacetamide-pyridine-sulfur dioxide and phosphorus pentoxide A further illustration of the relationship between the unsaturated and saturated lactones of this invention is shown by the following conversion:

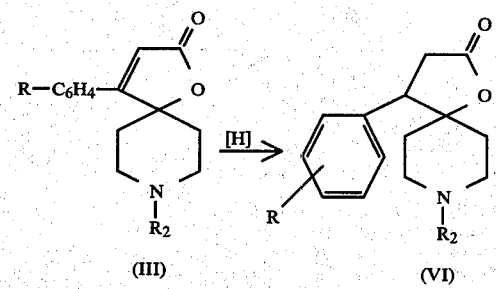

wherein R and $R_2$ are as previously described. By this reaction the unsaturated lactone (III) is reduced to give the saturated lactone (VI). Treatment with hydrogen and a palladium catalyst are suitable conditions. The saturated lactone thereby obtained is identical in all respects with the saturated lactone prepared by the previously described methods.

A preferred embodiment of the present invention may be represented by the following general formula:

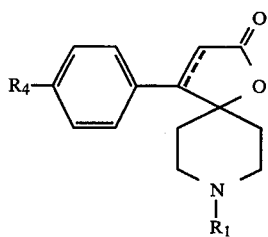

wherein

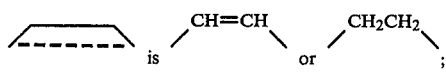

$R_1$ is as hereinbefore defined; and $R_4$ is hydrogen or fluoro.

The compounds of the present invention are physiologically active on the central nervous system and show high activity as anti-psychotic or neuroleptic agents; and also as analgesic agents. A useful test for antipsychotic activity consists of measuring the reduction of spontaneous motor activity in animals. The use of reduced motor activity as a measure of neuroleptic activity has been described by Gray et al., Arch. Int. de Pharmacodyn, et de Therapie 134, 198–215 (1961) and by Kinnard et al, J. Pharmacol and Exp. Ther. 121, 354–361 (1957). The test compounds are administered orally to groups of four rats at the maximum tolerated dose with the compound dissolved or suspended in a starch vehicle. At an estimated time of peak effect, animals are placed singly into an activity counter (Amimex ®, Farad Electronics, Sweden) and the activity of each rat is recorded for a 5-minute period. The activity counts are compared to historical or parallel control values to determine significant decrease in locomotor activity. The compound is considered an active depressant if the counts are 50% or less of control values. When tested by the above described neuroleptic screening procedure, the typical compounds of the present invention listed in Table I showed neuroleptic activity.

TABLE I

| Neuroleptic screening (Motor Activity) | |
|---|---|
| Compound | Result |
| 4-(p-Fluorophenyl)-1-oxa-8-azaspiro-[4,5]dec-3-en-2-one, hydrochloride | Active |
| 4-(p-Fluorophenyl)-8-methyl-1-oxa-8-azaspiro[4,5]dec-3-en-2-one, hydrochloride | Active |
| 4-(p-Fluorophenyl)-8-phenethyl-1-oxa-8-azaspiro[4,5]dec-3-en-2-one, hydrochloride | Active |
| 8-Allyl-4-(p-fluorophenyl)-1-oxa-8-azaspiro[4,5]dec-3-en-2-one, hydrochloride | Active |
| 8-Cyclopropylmethyl-4-(p-fluorophenyl)-1-oxa-8-azaspiro[4,5]dec-3-en-2-one, hydrochloride | Active |
| 8-Benzyl-4-(p-fluorophenyl)-1-oxa-8-azaspiro[4,5]dec-3-en-2-one, hydrochloride | Active |
| 8-[3-(p-Fluorobenzoyl)propyl]-4-(p-fluorophenyl)-1-oxa-8-azaspiro[4,5]dec-3-en-2-one, hydrochloride | Active |
| 4-(p-Fluorophenyl)-8-(3-phenylpropyl)-1-oxa-8-azaspiro[4,5]dec-3-en-2-one, | |

TABLE I-continued

| Neuroleptic screening (Motor Activity) | |
|---|---|
| Compound | Result |
| hydrochloride | Active |

Additionally, neuroleptic screening may also be carried out by the antagonism of amphetamine lethality in grouped mice [see P. A. J. Janssen, et al., Arzneim,- Forsch. 15, 104 (1965)]. Known antipsychotics such as chorpromazine and haloperidol protect grouped mice from the lethal effects of d-amphetamine sulfate. Other types of "tranquilizers" such as Librium ® and Valium ® are ineffective. Groups of 10 mice are treated orally with the test compounds at a dose of 2 to 20 mg./kg. of body weight. After periodic absorption times the mice are subsequently given intraperitoneal injections of d-amphetamine sulfate at a dose of 15 mg./kg. of body weight. The time of peak effect is established as the absorption time for the respective compounds that protect the greatest percentage of mice from death within 24 hours, with equal to or greater than 50% protection being considered active. The results with a typical compound of this invention appear in Table II below.

TABLE II

| Neuroleptic Screening (Grouped Amphetamine Lethality) | |
|---|---|
| Compound | Result |
| 8-[4,4-bis(p-Fluorophenyl)butyl]-4-(p-fluorophenyl)-1-oxa-8-azaspiro[4,5]-dec-3-en-2-one, hydrochloride | Active |

Analgesic screening by reversal of abnormal walking gait in rats is carried out as follows: This is a modification of the method of D. C. Atkinson and A. Cowan, J. Pharm. Pharmacol. 26, 727 (1974). Male, albino Wistar strain rats, weighing 120–150 g. are deprived of food for about 5 hours. A 40% suspension of Brewer's yeast in physiological saline is injected, at a concentration of 0.25 ml./rat, into the plantar surface of the left hind paw of each rat. Groups of 3 to 5 or more rats are used for each test group. Three hours later, at which time an inflammation of the injected paw has developed, a pre-drug assessment of walking gait is made for each rat according to the following scoring system:

0 = Normal gait in the presence of a severely inflamed paw. There is continuous use of the foot pad.
0.5 = As above with intermittent mild limping.
1.0 = Constant limping, but continuous use of the foot pad.
1.5 = Limping with occasional three-legged gait (paw kept off walking surface) or intermittent use of digits in combination with foot pad.
2.0 = Continuous three-legged gait and/or only the tips of the digits touch the walking surface. There is no use of the foot pad.

More than 95% of the rats exhibit a gait score of 2.0 before being given a test compound. Compounds, in a suitable vehicle, are administered orally by gavage in a volume of 0.5 ml/100 g. of body weight. One and/or two hours later a post-drug assessment of walking gait is made as described above. The criterion of an analgesic response for each rat is a significant reduction of the post-drug score compared to the pre-drug score. For example, a score of 1.0 represents a 50% reversal of the abnormal gait, and a score of zero represents 100% reversal of the impaired gait produced by injection of brewer's yeast into the hind paw. The inflamed paw has increased sensitivity to painful stimuli resulting in the readily observed abnormal gait.

Post-treatment scores are measured for each animal (groups of 3 to 5 or more) and compared with the pretreatment determinations. These results may then be used for determination of screening activity, for dose-response estimates of potency, etc. For example, when a screening procedure is carried out using 3 rats per dose, the pretreatment score is 6.0 (2.0×3) and a post-treatment score of 4 (for 3 animals) may be considered as significant analgesic activity over parallel controls (starch vehicle). Another criterion for an analgesic effect in an individual animal may be considered as 50% or more reversal of the abnormal gait (score ≦ 1.0). These procedures are standardized for statistical significance, and are used for screening and/or dose-response and evaluation studies using methods well known to those skilled in the art. The results of this test on representative compounds of the present invention appear in Table III.

TABLE III

| Compound | Analgesic Screening (abnormal walking gait) Result |
|---|---|
| 4-(p-Fluorophenyl)-8-methyl-1-oxa-8-azaspiro[4,5]dec-3-en-2-one, hydrochloride | Active |
| 4-(p-Fluorophenyl)-8-phenethyl-1-oxa-8-azaspiro[4,5]dec-3-en-2-one, hydrochloride | Active |
| 8-Allyl-4-(p-fluorophenyl)-1-oxa-8-azaspiro[4,5]dec-3-en-2-one, hydrochloride | Active |
| 8-(Cyclopropylmethyl)-4-(p-fluorophenyl)-1-oxa-8-azaspiro[4,5]dec-3-en-2-one, hydrochloride | Active |
| 8-(p-Fluorophenyl)-8-(3-phenylpropyl)-1-oxa-8-azaspiro[4,5]dec-3-en-2-one, hydrochloride | Active |

The novel compounds of the present invention may be orally administered in compositions such as tablets wherein the principal active ingredient is mixed with conventional tableting ingredients such as corn starch, lactose, sucrose, sorbitol, talc, stearic acid, magnesium stearate, dicalcium phosphate, gums or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac and cetyl alcohol, cellulose acetate and the like. A particularly advantageous enteric coating comprises a styrene maleic acid copolymer together with known materials contributing to the enteric properties of the coating. The liquid forms in which the novel compounds of the present invention may be incorporated for administration include suitably flavored emulsions with edible oils, such as, cottonseed oil, sesame oil, coconut oil, peanut oil, and the like, as well as elixirs and similar pharmaceutical vehicles.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent, carrier or vehicle. The dosage may vary from about 0.1 to about 70 mg. per kg. of body weight. The daily dosage requirement may be from about 10 to about 1000 mg.. The specification for the novel dosage forms are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accordance with this invention are tablets, capsules, pills, powder packets, granules, wafers, cachets, teaspoonfuls, dropperfuls, segregated multiples of any of the foregoing and other forms as herein described.

Certain of the novel spirolactones of the present invention are also active analgesics when measured by the "writhing syndrome" test for analgesic activity as described by Siegmund, et al., Proc. Soc. Exp. Bio. and Med., 95, 729 (1957), with modifications. This method is based upon the reduction of the number of writhes following the intraperitoneal injection of one mg./kg. of body weight of phenyl-p-quinone in male Swiss albino mice weighinging 18–25 g. The syndrome is characterized by intermittent contractions of the abdomen, twisting and turning of the trunk, and extension of the hind legs beginning 3 to 5 minutes after injection of the phenyl-p-quinone. The test compounds are administered orally at screening doses of 100 or 200 mg./kg. to groups of 2 mice each, 30 minutes before injection of the phenyl-p-quinone. The total number of writhes exhibited by each group of mice is recorded for a 3 minute period commencing 15 minutes after injection of the phenyl-p-quinone. A compound is considered active if it reduces the total number of writhes in 2 test mice from a control value of approximately 30 per pair to a value of 18 or less. Table IV summarizes the results of this test on representative compounds of this invention.

TABLE IV

| Compound | Analgesic Screening (antiwrithing) Result |
|---|---|
| 4-(p-Fluorophenyl)-1-oxa-8-azaspiro-[4,5]dec-3-en-2-one, hydrochloride | Active |
| 4-(p-Fluorophenyl)-8-methyl-1-oxa-8-azaspiro[4,5]dec-3-en-2-one | Active |
| 8-Phenethyl-4-phenyl-1-oxa-8-azaspiro-[4,5]decan-2-one, hydrochloride | Active |
| 8-Methyl-4-phenyl-1-oxa-8-azaspiro-[4,5]decan-2-one, hydrochloride | Active |
| 8-(3-p-Fluorobenzoylpropyl)-4-phenyl-1-oxa-8-azaspiro[4,5]decan-2-one, hydrochloride | Active |
| 8-Acetyl-4-(p-fluorophenyl)-1-oxa-8-azaspiro[4,5]decan-2-one | Active |

A preferred embodiment of the present invention may be represented by the following structural formula:

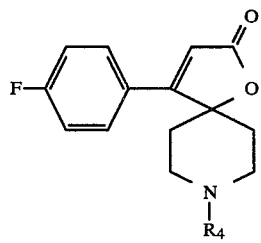

wherein R$_4$ is alkyl having up to 4 carbon atoms, alkenyl having from 3 to 6 carbon atoms, cycloalkylmethyl having from 4 to 7 carbon atoms or phenylalkyl having from 7 to 10 carbon atoms; and the pharmacologically acceptable non-toxic acid-addition salts thereof.

The invention will be described in greater detail in conjunction with the following specific examples.

EXAMPLE 1

8-Acetyl-4-(p-fluorophenyl)-1-oxa-8-azasprio[4,5]dec-3-en-2-one

A mixture of 115 g. of 1-acetyl-4-(p-fluorobenzoyl)-piperidine, 40–50% from isonipecotic acid, prepared by the method of R. L. Duncan, Jr.; et al; J. Med. Chem. 13, 1 (1970), 169.5 g. of ethyl bromoacetate, 67 g. of activated zinc(granular, 20–30 mesh, washed with 5% hydrochloric acid, water, acetone, ether, and dried at 65° C. for 15 minutes) and 575 ml. of methylene chloride is heated and stirred until a vigorous reaction is started. The heat source is removed and the exothermic reaction is controlled by use of an ice bath. When the reaction subsides, the mixture is heated under reflux for 3 hours then is poured into 5% hydrochloric acid and ice. The product is extracted into methylene chloride and the solvent is evaporated to provide a gum. The gum is dissolved in methylene chloride and the solution is passed through a column of alumina (Woelm, Activity II). The eluate is evaporated to give 100 g. of 1-acetyl-β(p-fluorophenyl)-4-piperidinehydracrylic acid, ethyl ester. A 750 ml. amount of concentrated sulfuric acid is added slowly with swirling to the above product. Considerable heat develops (exothermic reaction) and the temperature reaches about 80° C. The mixture is then stirred for 5 hours and is poured onto ice. The product is extracted into methylene chloride. The solution is dried, then is passed through a column of 1 kg. of alumina (Woelm, Activity II). The eluate is evaporated and the crystalline residue is collected with the aid of diethyl ether. The product of the example is recrystallized from ethanol to yield 53 g. m.p. 190°–192° C.

EXAMPLE 2

8-Substituted-4-(p-fluorophenyl)-1-oxa-8-azaspiro[4,5]-dec-3-en-2-ones

A. General Procedure for N-decarbethoxylation and N-deacetylation.

The N-carbethoxy or N-acetyl unsaturated spirolactone (1 g.), Example 1, and dilute hydrochloric acid (20 ml.; 6 N) are heated on the steam bath overnight. The resulting solution is evaporated to give the secondary amine as its hydrochloride salt. This is usually collected with the aid of ether and crystallized from an appropriate solvent.

B. General Procedure for the Preparation of N-substituted Spirolactones.

The above NH-spirolactone (3 g.), an alkylating agent (6 ml., or 6 g. of a solid), anhydrous potassium carbonate (6 g.) and sodium-dried benzene (75 ml.) are stirred and heated under reflux until thin layer chromatography (40% acetone in hexane) indicates the reaction is complete (usually overnight). Water is then added and the mixture is shaken thoroughly and the layers are separated. The aqueous layer is extracted thoroughly with methylene chloride and this is combined with the benzene layer. After drying, the solvent is evaporated to give the product. The hydrochloride salt is prepared by adding an excess of alcoholic hydrogen chloride to the base and is isolated by either addition of ether to cause separation of the salt or by evaporation of solvent followed by crystallization of the residue.

Following the above general procedures and using the compound of Example 1 the following derivatives listed in Table V are prepared:

TABLE V

| Compound Product of Reaction A or B | Procedure (A) = Deacetylating Agent Procedure (B) = Alkylating Agent | Recrystallization Solvent* | Melting Point °C. |
|---|---|---|---|
| 4-(p-Fluorophenyl)-1-oxa-8-azaspiro[4,5]dec-3-en-2-one, hydrochloride | (A) Dilute Hydrochloric Acid | CE | 272–274 |
| 4-(p-Fluorophenyl)-8-methyl-1-oxa-8-azaspiro[4,5]dec-3-en-2-one, hydrochloride | (B) Methyl iodide | CE | 297 |
| 4-(p-Fluorophenyl)-8-phenethyl-1-oxa-8-azaspiro[4,5]dec-3-en-2-one, hydrochloride | (B) Phenethyl bromide | CE | 272–274 |
| 8-Allyl-4-(p-fluorophenyl)-1-oxa-8-azaspiro[4,5]dec-3-en-2-one, hydrochloride | (B) Allyl bromide | ET | 264–265 |
| 8-(Cyclopropylmethyl)-4-(p-fluorophenyl)-1-oxa-8-azaspiro[4,5]dec-3-en-2-one, hydrochloride | (B) Cyclopropylmethyl bromide | M | 308–310 |
| 8-Benzyl-4-(p-fluorophenyl)-1-oxa-8-azaspiro[4,5]dec-3-en-2-one, hydrochloride | (B) Benzyl bromide | M | 290–291 |
| 8-[p,4-bis(p-Fluorophenyl)butyl]-4-(p-fluorophenyl)-1-oxa-8-azaspiro[4,5]dec-3-en-2-one, hydrochloride | (B) 1-Chloro-4,4-di(p-fluorophenyl)butane | M | 146–149 |
| 8-[3-(p-Fluorobenzoyl)propyl]-4-(p-fluorophenyl)-1-oxa-8-azaspiro[4,5]dec-3-en-2-one, hydrochloride | (B) 3-(p-Fluorobenzoyl)propyl chloride | M | 287–288 |
| 4-(p-Fluorophenyl)-8-(3-phenylpropyl)-1-oxa-8-azaspiro[4,5]dec-3-en-2-one, hydrochloride | (B) 3-Phenylpropyl bromide | ET | 266–268 |
| 4-(p-Fluorophenyl)-8-α-methylbenzyl-1-oxa-8-azaspiro[4,5]dec-3-en-2-one | (B) α-Methylbenzyl bromide | A-H | 129–132 |

TABLE V-continued

| Compound Product of Reaction A or B | Procedure (A) = Deacetylating Agent<br>Procedure (B) = Alkylating Agent | Recrystallization Solvent* | Melting Point °C. |
|---|---|---|---|
| 8-Benzoylmethyl-4-(p-fluorophenyl)-1-oxa-8-azaspiro[4,5]dec-3-en-2-one hydrochloride | (B) Phenacyl bromide | M | 290–292 |

*A = Acetone; CE = Collected with Ether; ET = Ethanol; H = Hexane; M = Methanol

EXAMPLE 3

8-Substituted-4-(p-fluorophenyl)-1-oxa-8-azaspiro[4,5]decan-2-ones

About 5 g. of the appropriate unsaturated lactone (III), 1 g. of 10% palladium-on-charcoal, and 200 ml of ethanol are hydrogenated in a Parr apparatus (initial pressure about 22 lbs/sq. in.). After 18 hours the reduction is complete, the mixture is filtered, and the filtrate evaporated to a solid residue and collected with the aid of ether. The saturated lactone (VI), thereby obtained (ca 90%), is used without purification in further transformations or purified by recrystallization from a suitable solvent, such as acetone/hexane. If desired, a suitable acid addition salt may be prepared (when $R_2$ is not acyl).

Following these general procedures, the reductions described in Table VI are carried out:

TABLE VI

| 8-Substituted-4-(p-fluorophenyl)-1-oxa-8-azaspiro[4,5]dec-3-en-2-ones(unsaturated spirolactones) | 8-Substituted-4-(p-fluorophenyl)-1-oxa-8-azaspiro[4,5]decan-2-ones(saturated spirolactones) |
|---|---|
| 8-Acetyl-4-(p-fluorophenyl)-1-oxa-8-azaspiro[4,5]dec-3-en-2-one, mp 190–192° C. | → 8-Acetyl-4-(p-fluorophenyl)-1-oxa-8-azaspiro[4,5]decan-2-one, mp 140–141° C. |
| 4-(p-Fluorophenyl)-1-oxa-8-azaspiro[4,5]dec-3-en-2-one hydrochloride, mp 272–274° C. | → 4-(p-Fluorophenyl)-1-oxa-8-azaspiro[4,5]decan-2-one hydrochloride, mp 298–300° C. |
| 8-Phenethyl-4-(p-fluorophenyl)-1-oxa-8-azaspiro[4,5]dec-3-en-2-one hydrochloride, mp 272–274° C. | → 8-Phenethyl-4-(p-fluorophenyl)-1-oxa-8-azaspiro[4,5]decan-2-one hydrochloride, mp 288–289° C. |

EXAMPLE 4

8-Substituted-4-phenyl-1-oxa-8-azaspiro[4,5]dec-3-en-2-ones

The above general procedures of Examples 1, 2 and 3 are repeated and the following derivatives listed in Table VII are prepared:

TABLE VII

| Compound | Procedure (A) = Cyclization; H₂SO₄ (Example 1)<br>(B) = Deacylation (Example 2)<br>(C) = Alkylation (Example 2)<br>(D) = Reduction (Example 3) |
|---|---|
| 8-Carbethoxy-4-phenyl-1-oxa-8-azaspiro[4,5]dec-3-en-2-one | (A) Concd. H₂SO₄; 80° C. |
| 8-Carbethoxy-4-phenyl-1-oxa-8-azaspiro[4,5]decan-2-one | (D) H₂; Pd-on-carbon |
| 8-Acetyl-4-(m-chlorophenyl)-1-oxa-8-azaspiro[4,5]dec-3-en-2-one | (A) Concd. H₂SO₄; 80° C. |
| 4-(m-Chlorophenyl)-1-oxa-8-azaspiro[4,5]dec-3-en-2-one | (B) 6 N Hcl; 80°; ca 20 hr. |
| 8-Phenethyl-4-(m-chlorophenyl)-1-oxa-8-azaspiro[4,5]dec-3-en-2-one | (C) Phenethyl bromide |
| 8-Cyclopropylmethyl-4-(m-chlorophenyl-1-oxa-8-azaspiro[4,5]dec-3-en-2-one | (C) Cyclopropylmethyl bromide |
| 8-Phenethyl-4-(m-chlorophenyl)-1-oxa-8-azaspiro[4,5]decan-2-one | (D) H₂(1 mole); Pd-on-carbon |
| 8-Acetyl-4-(α,α,α-trifluoro-m-tolyl)-1-oxa-8-azaspiro[4,5]dec-3-en-2-one | (A) Concd. H₂SO₄; 80° C. |
| 4-(α,α,α-Trifluoro-m-tolyl)-1-oxa-8-azaspiro[4,5]dec-3-en-2-one | (A) 6 N HCl; 80° C.; ca 20 hr. |
| 8-Methyl-4-(α,α,α-trifluoro-m-tolyl)-1-oxa-8-azaspiro[4,5]dec-3-en-2-one | (C) Methyl iodide |
| 8-[3-(p-Fluorobenzoyl)propyl]-4-(α,α,α-trifluoro-m-tolyl)-1-oxa-8-azaspiro[4,5]dec-3-en-2-one hydrochloride | (C) 3-(p-Fluorobenzoyl)propyl chloride |
| 8-Acetyl-4-(o-chlorophenyl)-1-oxa-8-azaspiro[4,5]dec-3-en-2-one | (A) Concd. H₂SO₄; 80° C. |
| 8-Acetyl-4-(p-fluorophenyl)-1-oxa-8-azaspiro[4,5]decan-2-one | (A) Concd. H₂SO₄; room temperature (See Example 6) |
| 8-[3-(p-Fluorophenyl)propyl]-4-(p-fluorophenyl-1-oxa-8-azaspiro[4,5]dec-3-en-2-one | (C) 3-(p-Fluorophenyl)propyl bromide |

EXAMPLE 5

8-Carbethoxy-4-phenyl-1-oxa-8-azaspiro[4,5]decan-2-one

To a stirred suspension of 40 g. of sodium hydride (50% in oil) in 400 ml. of sodium-dried benzene, is added 120 ml. of diethyl carbonate and the mixture is heated to the reflux temperature. A solution of 20 g. (0.75 mol) of 4-acetyl-4-phenylpiperidine in 80 ml. of sodium-dried benzene is then added and the refluxing continued for about 24 hours. The mixture is cooled in an ice-bath, the excess sodium hydride decomposed by the cautious addition of ethanol, and a large volume of hexane is added. The precipitate which forms is collected, and washed thoroughly with hexane. This material is added, portionwise with stirring, to an ice-cold mixture of 1 liter of 5% hydrochloric acid and 500 ml. of methylene chloride. When the mixture is dissolved the layers are separated and the organic layer is dried (anhyd. $Na_2SO_4$) and evaporated. The residue, an oil, is dissolved in methylene chloride and passed through a short column of alumina (Woelm, neutral, Activity II). Evaporation of the eluate gives 1-carboxy-$\beta$-oxo-4-phenyl-4-piperidinepropionic acid diethyl ester as a oil which is sufficiently pure for the next step; this product gives a positive $FeCl_3$ test.

A solution of 2.12 g (0.056 mol) of sodium borohydride in ethanol (193 ml.) is added dropwise with stirring to a cold solution (0°–5° C.) of 19.25 g. (0.055 mol) of the above $\beta$-oxo-piperidinepropionic ester. Stirring and cooling is continued for 5 hours and the mixture is diluted with water. The product is extracted into methylene chloride and isolated as a crude oil after evaporation of the solvent; 1-carboxy-4-phenyl-4-piperidinehydracrylic acid diethyl ester is thereby obtained. The compound has $\lambda KBr_{max}$ 5.75 and 5.9 $\mu$(IR), and gives a negative $FeCl_3$ test; it is sufficiently pure for the next step.

One gram of the above 4-phenyl-4-piperidinehydracrylic ester and 50 g. of polyphosphoric acid are heated on the steam bath for 6 hours. The mixture is then poured into ice and water, and the product extracted into methylene chloride. The organic layer is washed with water, dried (anhyd. $Na_2SO_4$) and evaporated to a residual gum. This is purified by dissolving it in methylene chloride, passing the solution through a short column of alumina (Woelm, Activity II), and evaporation of the eluate to give the product of the example as a gum. IR and NMR spectra indicate this product is identical with the saturated spirolactone obtained in crystalline form by the procedures described below in Example 6.

EXAMPLE 6

8-Carbethoxy-4-phenyl-1-oxa-8-azaspiro[4,5]decan-2-one

A mixture of 0.5 g. of the 1-carboxy-4-phenyl-4-piperidinehydracrylic acid diethyl ester described above (Example 5) and 5 ml of concentrated sulfuric acid is warmed on the steam bath for 15 minutes. The solution is poured onto ice and the product extracted into methylene chloride. The residue obtained by evaporation of solvent is triturated with diethyl ether; the precipitate is collected and is substantially pure 4-(3-oxo-1-indanylidene)-1-piperidinecarboxylic acid ethyl ester, mp. 117°–120° C. Hexane is added to the filtrate and the precipitate which forms is collected; essentially pure saturated spirolactone, mp. 110°–112° C., the product of the example is thereby obtained. Infrared (IR) and NMR spectra of these compounds are identical, respectively, with those of the same compounds prepared by the alternate procedure below.

1-Carboxy-$\beta$-phenyl-4-piperidinehydracrylic acid diethyl ester (60 g, 0.17 mol; mp 73°–75° C.), prepared by the general procedures described in Example 1, is added portionwise to a stirred mixture of 600 ml of concentrated sulfuric acid, and stirring at room temperature is continued for 4 hours. The solution is poured onto ice, and the mixture is extracted with a copious volume of diethyl ether. The ether extract is washed with water, dried and evaporated; the residue is collected as a solid (34 g) with the aid of a small volume of ether. This product mixture is purified by partition chromatography on a Celite® diatomaceous earth column developed with a hexane-methanol solvent system. The two main fractions separated on the partition column are each, in methylene chloride solution, passed through a short column of alumina (Woelm, Activity II) and the columns are eluted with methylene chloride and then with ethylacetate. Evaporation of the eluates gives the two products described above. The more polar product is the saturated spirolactone product of the example (17 g); mp. 112°–114° C. Recrystallization from acetone-hexane gives analytically pure material, mp. 121°–122° C. The second product, present in lesser amount, is the less polar 4-(3-oxo-1-indanylidene)-1-piperidinecarboxylic acid ethyl ester described above, mp. 118°–122°; recrystallization from aqueous methanol gives the analytical sample, mp. 114°–116° C.

EXAMPLE 7

8Carbethoxy-4-phenyl-1-oxa-8-azaspiro[4,5]decan-2-one

A solution of the 1-carboxy-4-phenyl-4-piperidinehydracrylic acid diethyl ester (1 g), described in Example 5, in 50 ml of sodium-dried benzene is treated with 10 g of phosphorus pentoxide and the mixture is heated under reflux for 4 hours. The benzene layer is decanted, washed with water, dried, and evaporated to give 0.5 g. of 1-carboxy-1,2,3,6-tetrahydro-$\beta$-phenyl-4-pyridinepropionic acid diethyl ester as a gum, identified by its IR, NMR, and UV spectra.

The same tetrahydro-pyridinepropionic ester is also obtained when the same phenyl-piperidinehydracrylic ester (0.2 g) above is treated with N-bromoacetamide (0.12 g) and pyridine (2.5 ml). The resulting solution is kept in the dark at room temperature for 15 minutes, cooled in ice and sulfur dioxide is bubbled through until a negative starch-iodide test is obtained. Water is added, the mixture is extracted with methylene chloride, the organic layer dried and evaporated, and the above tetrahydropyridinepropionic ester is obtained as a gum with the identical IR spectrum.

This 1-carboxy-1,2,3,6-tetrahydro-$\beta$-phenyl-4-pyridinepropionic acid diethyl ester (0.1 g) and 1 ml of concentrated sulfuric acid are warmed on the steam bath for 2.5 hours. Ice is added followed by water, and the mixture is extracted with methylene chloride. The organic layer is washed with water again, dried and evaporated to give the product of the example as a gum; its IR spectrum is identical with that of the same saturated spirolactone product described in Example 6.

EXAMPLE 8

8-Substituted-4-phenyl-1-oxa-8-azaspiro[4,5]decan-2-ones

The general procedures of Example 2 are repeated using, as the starting material, the 8-carbethoxy-4-phenyl-1-oxa-8-azaspiro[4,5]decan-2-one product of Examples 5, 6 and 7. The products obtained are described in Table VIII, together with the alkylation procedure used to obtain the individual compound listed.

TABLE VIII

| Compound | (A) = Deacylation<br>Procedure (B) = Alkylation |
|---|---|
| 4-Phenyl-1-oxa-8-azaspiro[4,5]decan-2-one hydrochloride, mp. 296–297° C. | (A) 6 N HCl; 80° C.; 20 hr. |
| 8-Phenethyl-4-phenyl-1-oxa-8-azaspiro-[4,5]decan-2-one hydrochloride, mp. 265–267° C. | (B) Phenethyl bromide |
| 8-Methyl-4-phenyl-1-oxa-8-azaspiro-[4,5]decan-2-one hydrochloride, mp. 252–254° C. | (B) Methyl iodide |
| 8-[3-(p-Fluorobenzoyl)propyl]-4-phenyl-1-oxa-8-azaspiro[4,5]decan-2-one hydrochloride, mp. 196–197° C. | (B) 3-(p-Fluorobenzoyl)propyl chloride |

We claim:

1. A compound selected from the group consisting of those of the formulae:

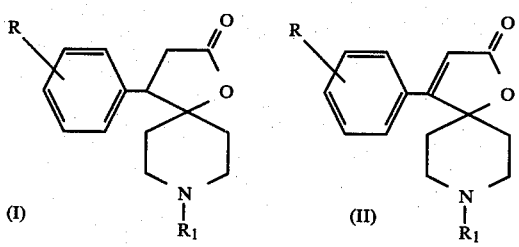

wherein R is hydrogen, fluoro, chloro or trifluoromethyl and $R_1$ is hydrogen, alkyl having up to 4 carbon atoms, alkanoyl having up to 4 carbon atoms, alkenyl having from 3 to 6 carbon atoms, cycloalkylmethyl having from 4 to 7 carbon atoms, phenylalkyl having from 7 to 10 carbon atoms, ω-benzoylalkyl having from 8 to 11 carbon atoms, ω-(p-fluorophenyl)alkyl having from 7 to 10 carbon atoms, ω-di (p-fluorophenyl)alkyl having from 13 to 16 carbon atoms or ω-(p-fluorobenzoyl)alkyl having from 8 to 11 carbon atoms; and the pharmacologically acceptable acid-addition salts thereof.

2. The compound according to claim 1, formula (II) thereof, wherein R is para-fluoro and $R_1$ is hydrogen; 4-(p-fluorophenyl)-1-oxa-8-azaspiro[4,5]dec-3-en-2-one.

3. The compound according to claim 1, formula (II) thereof, wherein R is para-fluoro and $R_1$ is methyl; 4-(p-fluorophenyl)-8-methyl-1-oxa-8-azaspiro[4,5]dec-3-en-2-one.

4. The compound according to claim 1, formula (II) thereof, wherein R is para-fluoro and $R_1$ is β-phenethyl; 4-(p-fluorophenyl)-8-(2-phenylethyl)-1-oxa-8-azaspiro[4,5]dec-3-en-2-one.

5. The compound according to claim 1, formula (II) thereof, wherein R is para-fluoro and $R_1$ is allyl; 4-(p-fluorophenyl)-8-allyl-1-oxa-8-azaspiro[4,5]dec-3-en-2-one.

6. The compound according to claim 1, formula (II) thereof, wherein R is a para-fluoro and $R_1$ is cyclopropylmethyl; 4-(p-fluorophenyl)-8-cyclopropylmethyl-1-oxa-8-azaspiro[4,5]dec-3-en-2-one.

7. The compound according to claim 1, formula (II) thereof, wherein R is para-fluoro and $R_1$ is benzyl; 4-(p-fluorophenyl)-8-benzyl-1-oxa-8-azaspiro[4,5]dec-3-en-2-one.

8. The compound according to claim 1, formula (II) thereof, wherein R is para-fluoro and $R_1$ is 3-(para-fluorobenzoyl)propyl; 4-(p-fluorophenyl)-8-[3-(p-fluorobenzoyl)propyl]-1-oxa-8-azaspiro[4,5]dec-3-en-2-one.

9. The compound according to claim 1, formula (II) thereof, wherein R is para-fluoro and $R_1$ is 3-phenylpropyl; 4-(p-fluorophenyl)-8-(3-phenylpropyl)-1-oxa-8-azaspiro[4,5]dec-3-en-2-one.

10. The compound according to claim 1, formula (II) thereof, wherein R is para-fluoro and $R_1$ is ω-di(para-fluorophenyl)butyl; 4-(p-fluorophenyl)-8-[4,4-bis(p-fluorophenyl)butyl]-1-oxa-8-azaspiro[4,5]dec-3-en-2-one.

11. The compound according to claim 1, formula (I) thereof, wherein R is hydrogen and $R_1$ is β-phenethyl; 4-phenyl-8-(2-phenylethyl)-1-oxa-8-azaspiro[4,5]decan-2-one.

12. The compound according to claim 1, formula (I) thereof, wherein R is hydrogen and $R_1$ is methyl; 4-phenyl-8-methyl-1-oxa-8-azaspiro[4,5]decan-2-one.

13. The compound according to claim 1, formula (I) thereof, wherein R is hydrogen and $R_1$ is 3-(para-fluorobenzoyl)propyl; 4-phenyl-8-[3-(p-fluorobenzoyl)propyl]-1-oxa-8-azaspiro[4,5]decan-2-one.

14. The compound according to claim 1, formula (I) thereof, wherein R is para-fluoro and $R_1$ is acetyl; 4-(p-fluorophenyl)-8-acetyl-1-oxa-8-azaspiro[4,5]decan-2-one.

* * * * *